United States Patent [19]

Bassignana et al.

[11] Patent Number: 5,350,923
[45] Date of Patent: Sep. 27, 1994

[54] APPARATUS FOR USE WITH ANALYTICAL MEASURING INSTRUMENTS USING ELECTROMAGNETIC RADIATION ANALYSIS METHODS

[75] Inventors: Isabella C. Bassignana; Tibor F. I. Kovats, both of Ottawa, Canada

[73] Assignee: Northern Telecom Limited, Montreal, Canada

[21] Appl. No.: 996,411

[22] Filed: Dec. 23, 1992

Related U.S. Application Data

[63] Continuation-in-part of Ser. No. 833,470, Feb. 6, 1992, abandoned.

[51] Int. Cl.⁵ .............................................. H01J 37/20
[52] U.S. Cl. .................. 250/453.11; 378/79; 378/161; 356/244
[58] Field of Search .................. 250/453.11; 378/161, 378/70, 79, 80; 356/244

[56] References Cited

U.S. PATENT DOCUMENTS

| | | | |
|---|---|---|---|
| 3,973,120 | 8/1976 | Kessels | 378/80 |
| 4,115,689 | 9/1978 | Won | 378/79 |
| 5,161,179 | 11/1992 | Suzuki et al. | 378/161 |
| 5,181,233 | 1/1993 | Rink et al. | 378/79 |

*Primary Examiner*—Paul M. Dzierzynski
*Assistant Examiner*—Kiet T. Nguyen
*Attorney, Agent, or Firm*—Reginald J. Austin

[57] ABSTRACT

A method and apparatus for use in performing non-contact analytical evaluation of a semiconductor wafer, which needs to be kept clean, to be performed outside of clean room facilities. The apparatus maintains a clean environment surrounding the semiconductor wafer and a portion of the apparatus is substantially transparent to a probe beam of electromagnetic radiation such as X-rays and visible light. The invention substantially overcomes the expenses associated with locating analytical test equipment for testing semi-conductor wafers within clean room facilities.

9 Claims, 2 Drawing Sheets

APPARATUS FOR USE WITH ANALYTICAL MEASURING INSTRUMENTS USING ELECTROMAGNETIC RADIATION ANALYSIS METHODS

FIELD OF INVENTION

This invention relates to a method and apparatus for use in performing non-contact analytical evaluation of a semiconductor wafer and is a continuation-in-part of patent application bearing Ser. No. 07/833,470 and filed on Feb. 6, 1992, now abandoned.

BACKGROUND OF THE INVENTION

It is a well-known concern of individuals involved in semiconductor research and development that analytically evaluating semiconductor wafers within the confines of a clean room facility is an expensive and time consuming proposition. Test equipment occupies costly clean room floor space and special dress requirements for process monitoring personnel is both time consuming and inconvenient.

In greater detail, semiconductor wafers are manufactured in clean room environments during which non-contact and non-destructive analytical evaluations are performed to monitor process steps as required. Typically these analytical tests are performed in the confines of clean rooms having a class environment rating appropriate for the type of semiconductor devices being manufactured. The analysis can be by electromagnetic radiation such as X-rays or visible light. One typical example would be to determine the characteristics of a wafer surface after the completion of a particular process step. To prevent the contamination of a wafer, it must at all times during the manufacturing and process monitoring cycles be kept in a clean room environment.

Clean room facilities of the type required for modern semiconductor wafer manufacturing have been built utilizing the height of three stories of a building. Of these three stories, the clean room is typically the middle story and is sandwiched between two floors which house expensive air purification equipment. A portion of this expensive floor space is simply required for storing equipment which is needed for monitoring process steps and which obviously dictates the minimum floor space needed for the manufacturing of semiconductor wafers.

When working within a clean room environment all personnel are required to wear special clothing to help maintain the clean room environment. This clothing must be donned before entering the clean environment and removed after they leave. This is an inconvenient and time consuming process. In particular the process monitoring personnel who are required only for monitoring process steps must enter and exit the clean room environment many times daily.

Analysis methods may require special equipment which cannot be modified or adapted for use within clean room environments and therefore semiconductor wafers which are removed from the clean room environment for evaluation are typically thrown in the garbage once the evaluation is finished for fear of contamination. Equipment that is compatible with clean room environments is very expensive and even then must first be precleaned before being placed within the clean room environment. As well all equipment for use within the clean room environment must only use internal lubricants which are compatible for use within a clean room facility.

SUMMARY OF INVENTION

The present invention provides a method and apparatus for use in performing non-contact and non-destructive analytical evaluation of a semiconductor wafer and which seeks to overcome or minimize the above problems.

One aspect of the invention provides an apparatus for use in performing non-contact analytical evaluation of a semiconductor wafer, comprising a sealable container defining a chamber, which upon sealing the container is then isolated; the sealable container comprising: window means into the sealable container, the window means comprising a membrane of a substantially non-crystalline organic polymer, the window means being capable of allowing a probe beam of radiant energy of a particular wavelength suitable for non-contact analytical evaluation of the semiconductor wafer to pass therethrough into the isolated chamber while non-substantially affecting diffraction and attenuation of the beam and which is capable of passing radiant energy outwardly from the isolated chamber while non-substantially affecting the diffraction and attenuation of the radiant energy; and positioning means for positioning the semiconductor wafer within the isolated chamber in a location aligned with the window means to allow the probe beam of radiant energy to be directed through the window means at the semiconductor wafer and to allow radiant energy to pass outwardly from the semiconductor wafer within the chamber.

In use, the invention overcomes the expense of locating equipment for analytically evaluating semiconductor wafers within the confines of the clean room environment because the semiconductor wafer, protected from dust particle contamination is analytically evaluated outside the clean room environment. Equipment for use in performing analytical evaluation no longer needs to occupy costly clean room floor space and the precleaning of the equipment is not required. Process monitoring personnel are also no longer required to don and doff special suits and therefore a considerable amount of time is saved.

The window means may for example be made from any of the following polymers, i.e. poly-propylene, poly-isoprene, poly-vinyl chloride, poly-vinilydene fluoride, poly-carbonate, poly-methyl methacrylate, poly-ethylene, or nitro-cellulose. Attenuation is influenced by the thickness of the membrane. The choice of any non-crystalline organic polymer, including those mentioned in the last preceding sentence is dependent upon the maximum attenuation requirement of the user and whether a particular polymer may be made sufficiently thin to act as a membrane while satisfying those requirements. All of the polymers mentioned above are substantially transparent to X-rays and of the group; poly-carbonate, poly-methyl methacrylate, poly-ethylene, and nitro-cellulose are also transparent to ultra-violet, infra-red and visible light.

Preferably the window means comprises a membrane of nitro-cellulose polymer having a thickness in the order of three microns and having a uniformity of less than about ± 0.2 microns. A membrane having these characteristics exhibits an attenuation level to X=rays (1–2 Å) of less than about 1%. An apparatus according to the invention and having a preferred nitro-cellulose polymer membrane may be used for X-ray diffraction evaluation, photo-luminescence evaluation and photo-reflectance evaluation since it is substantially transparent to visible, ultra-violet and infra-red light as well as X-ray energy.

Preferably the area of the membrane of the window means is substantially larger than the surface area of the semiconductor wafer to be tested, by an amount sufficient to permit scanning of the complete wafer surface by test equipment having probe beams requiring predetermined incident angles other than ninety degrees.

Another aspect of the invention provides a method of evaluating a semiconductor wafer by non-contact analytical evaluation, comprising the steps of: in a first environment, inserting the semiconductor wafer into a chamber within an open container and positioning the semiconductor wafer in a location within the chamber, the container capable of being sealed to isolate the chamber from an outside environment, the container having window means into the chamber, the window means comprising a membrane of a substantially non-crystalline organic polymer, the window means being capable of allowing a probe beam of radiant energy of a particular wavelength suitable for non-contact analytical evaluation of the wafer, to pass there through while non-substantially affecting diffraction and attenuation of the beam, and which is capable of passing radiant energy outwardly from the isolated chamber while non-substantially affecting diffraction and attenuation of the radiant energy; sealing the container to isolate the chamber and the semiconductor wafer from the first environment with the semiconductor wafer aligned with the window means to enable the probe beam of radiant energy to be directed through the window means and at the semiconductor wafer; moving the sealed container into a second environment and with the chamber and semiconductor wafer isolated from the second environment; passing the probe beam of radiant energy through the window means at the semiconductor wafer during the performance of the non-contact analytical evaluation; and analyzing radiant energy from the semiconductor wafer which passes outwardly from the wafer within the chamber through the window means to determine characteristics about the semiconductor wafer.

BRIEF DESCRIPTION OF THE DRAWINGS

One embodiment of the invention will now be described, by way of example, with reference to the accompanying drawings in which.

DETAILED DESCRIPTION

Figure 1:
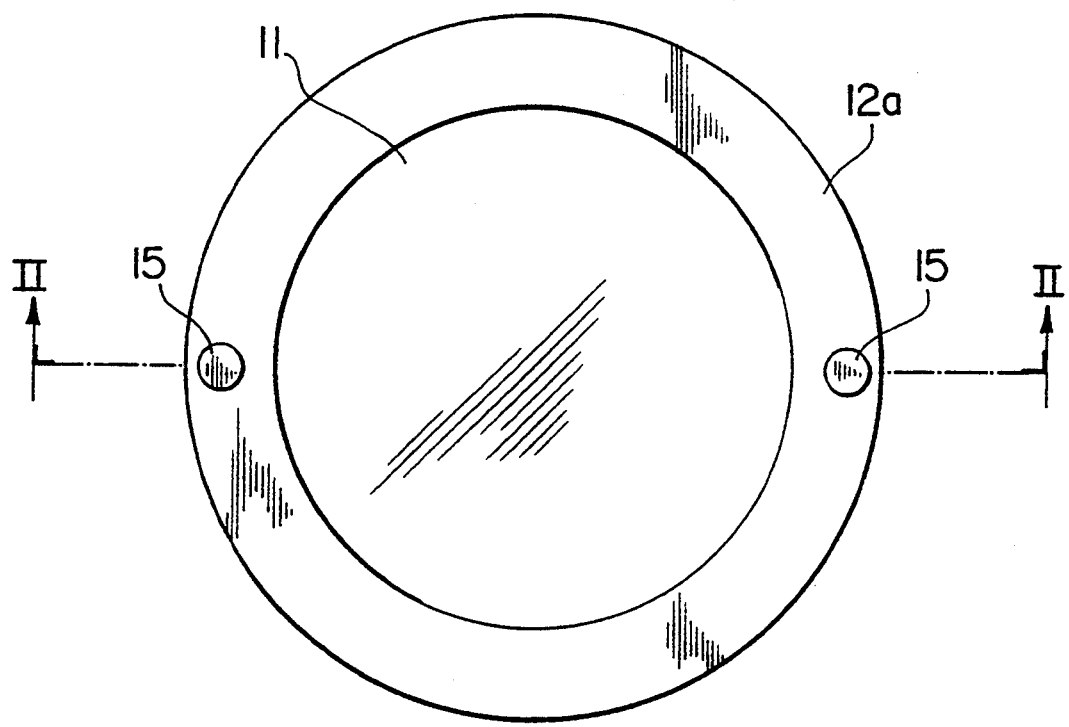
FIG. 1 is a plan view of an apparatus according to the embodiment.
Figure 2:
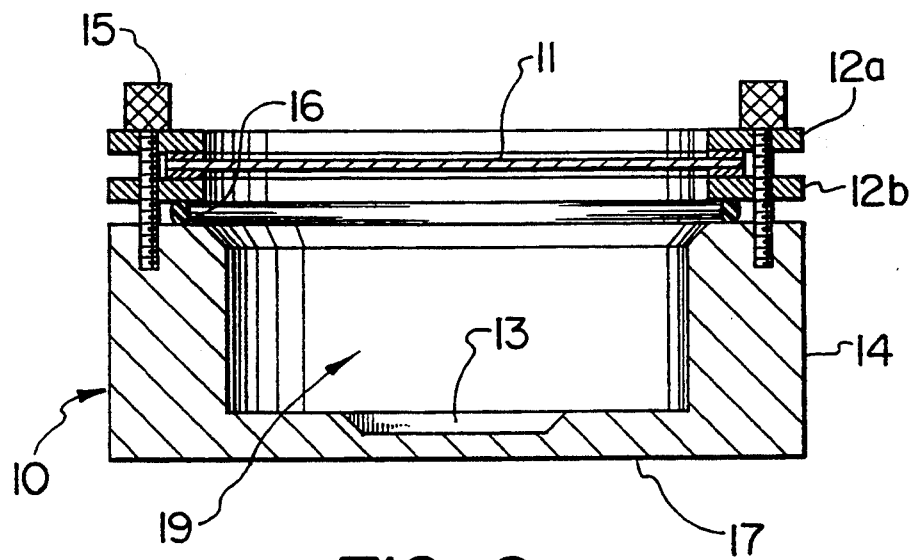
FIG. 2 is a cross sectional view of the apparatus of FIG. 1 and taken along line II—II in FIG. 1.

In the embodiment, as shown in FIGS. 1, 2 an apparatus 10 for use in performing non-contact analytical evaluation of a semiconductor wafer, comprises a machined aluminum base 14, in the form of a cylinder, the cylinder having a closed bottom end 17 and an open top end. The container includes window means in the form of a planar window 11 which may be releasably secured to the open end of the aluminum base 14 as shown in FIGS. 1 and 2 with the use of screw threaded means in the form of screws 15 to form an isolated chamber 19. Securing of the window 11 is effected by sandwiching continuous edge regions of the window between two concentric rigid rings 12a, 12b with the screws 15 received in threaded bores in the base 14. The chamber 19 is rendered airtight by a seal 16 in the form of an 'O' ring which is compressed between the bottom ring 12b and the open end of the aluminum base 14. A positioning means is included for positioning a semiconductor wafer. This is formed by a recessed cavity 13 in the cylinder end 17, the cavity diameter and location suitable for positioning the wafer in a predetermined position relative to the window 11.

For reasons of practicality a membrane material for the window 11 would be one that can be used in conjunction with a majority of the evaluations mentioned. A membrane to be used in conjunction with X-rays of a wavelength commonly used in X-ray diffraction analysis (1.54 Å) must be substantially non crystalline. The requirement that the membrane for the window 11 be non crystalline arises because X-rays can diffract as they pass through a medium having a crystal structure. A resulting detected diffraction pattern would then not be due solely to the wafer 20 but to a combination of the membrane and the wafer 20 under test. This alteration of the diffraction pattern due to the membrane would result in inaccurate conclusions about the wafer's composition.

A membrane for use with the invention is manufactured by Micro Lithography Incorporated of Sunnyvale California having a model number, PE 02-102-001. The membrane is composed of a nitrocellulose polymer having an absolute thickness of 2.85 microns and a uniformity of ± 0.2 microns. The membranes are available in various diameters. The membranes are inexpensive and are replaceable should one on an apparatus ever be punctured while being handled.

The base 14 of the embodiment is a charge conducting material. Any charge conducting material will suffice. Semiconductor wafers can be damaged by electric discharges between surfaces which are at different voltage potentials. A charge conducting base 14 for example would allow a technician wearing a ground strap to touch the apparatus 10 thus eliminating any potential difference between the container 10 and the technician.

An apparatus 10 having a membrane window 11 composed of for example a nitro cellulose polymer can be successfully used in conjunction with analytical equipment for X-ray diffraction analysis, photoluminescence, and photoreflectence testing of semiconductor wafers. The use of the apparatus can possibly be extended to include X-ray topography and reflectomerry analysis equipment. Modifications as to height of the window 11 from the wafer 20 surface and to the exposed area of the window 11 relative to the area of the wafer 20 may need to be considered for these uses.

In order to evaluate the wafer 20, in a clean room environment the wafer 20 is placed inside the apparatus 10 by locating the wafer 20 in the recessed cavity 13 of the bottom end 17 of the base 14. The window 11 is then positioned over the open end of the base 14 and the window 11 is secured airtightly in position by the use of the rings 12a, 12b and fastening screws 15 which compresses the 'O' ring seal 16 thus isolating the chamber 19 which isolates the wafer 20 from an environment outside the apparatus. The apparatus 10 is then removed from the clean room facility to allow the semiconductor wafer 20 to be evaluated using non-contact analytical test equipment located in a less clean environment.

Figure 3:
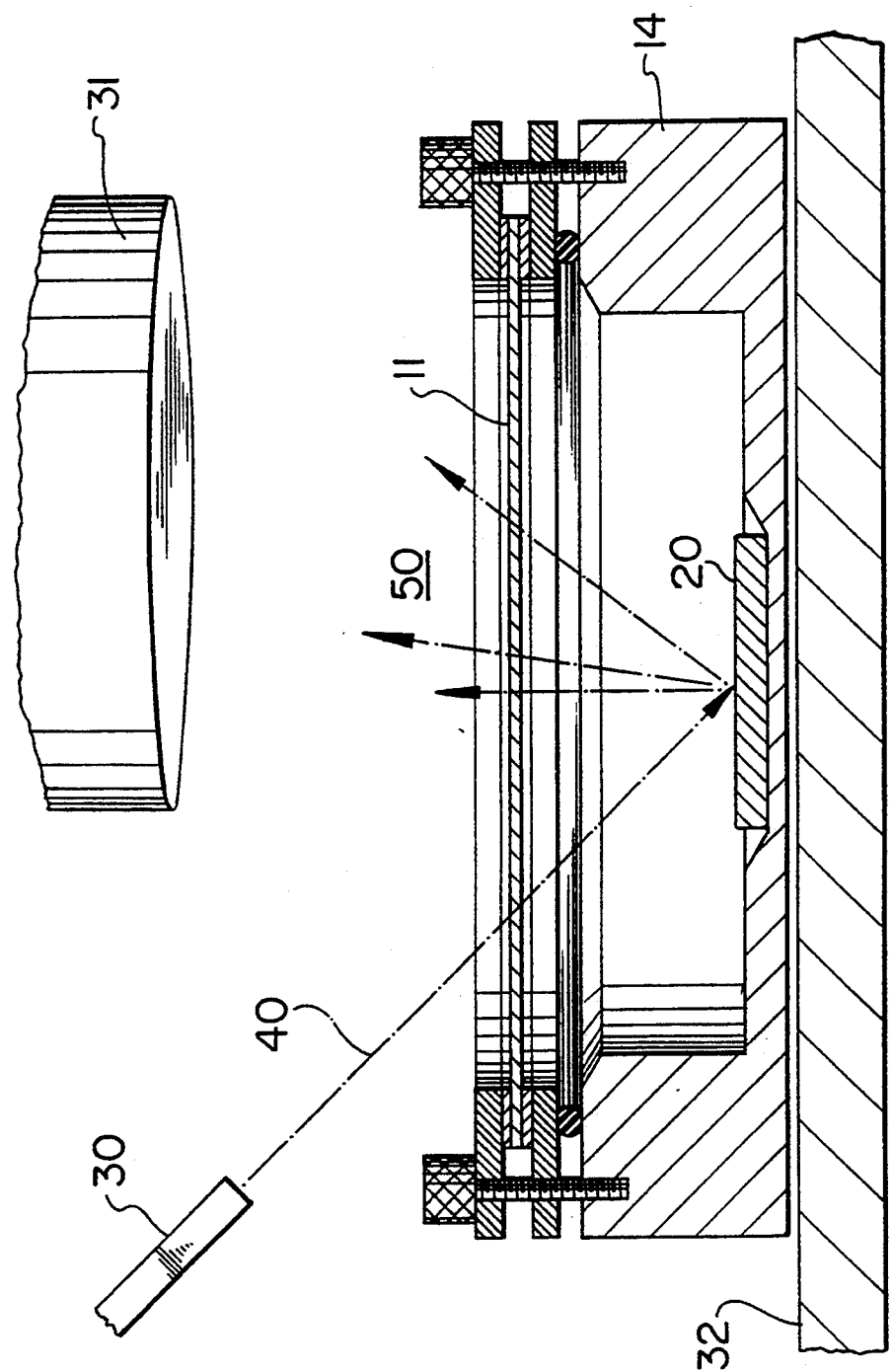
FIG. 3 is a view similar to FIG. 2, but to a larger scale, of the apparatus in use.

The apparatus 10 containing the wafer 20 is placed on a test instrument platform 32 to be used, as shown by FIG. 3, in conjunction with an analytical test instrument. The test instrument is an X-ray diffractometer and for clarity only the essential elements of the test instrument are shown. The test instrument comprises a transmitter 30 or source of an incident radiant energy beam 40 in conjunction with a receiver 31 for detecting returned energy 50 from a semiconductor wafer 20 located in the desired position in the cavity 13 .so as to be aligned with the window 11. The wafer 20 upper surface is then systematically irradiated from localized position to localized position with the beam 40 of incident radiant energy from the transmitter 30. Analysis of the returned energy 50 from the wafer identifies structure of the wafer 20 and hence it's composition. After analysis the apparatus 10 containing the wafer is returned to the clean room environment, the wafer then being removed from the apparatus for further processing.

At many stages during the manufacturing of semiconductor wafers it is desirable to conduct various analytical evaluations on the wafers to monitor manufacturing process steps. Typical evaluations for example may be by X-ray diffraction analysis, photoluminescence analysis or photoreflectence analysis of the semiconductor wafer. Each of the non-contact evaluations mentioned requires a probe beam of appropriate radiant energy to be incident on the surface of the wafer and the returned energy from the wafer 20 to be analyzed. Diffraction analysis requires a probe beam of X-rays while photoluminescence and photoreflectence testing both require probe beams having radiant energy in the visible light spectrum.

Photoluminescence testing, probes a semiconductor wafer with visible or ultraviolet light. The emitted radiation is usually in the visible or infrared portion of the electromagnetic spectrum. A window 11 to be used in photoluminescence analysis must then consist of a membrane which is substantially transparent to radiant energy within these three ranges of the electromagnetic spectrum. o Photoreflectence testing on the other hand uses a probe beam in the visible light spectrum and analyses returned energy also in the visible region of the spectrum.

The attenuation of an X-ray probe beam of a wavelength commonly used in diffraction analysis (1.54 Å) becomes negligible with a nitro-cellulose polymer membrane having an absolute thickness of about 3 microns and a uniformity of less than about ± 0.2 microns. Conveniently this same membrane is also substantially transparent to visible and ultraviolet light and only moderately attenuates infrared radiation thus allowing an apparatus having a nitrocellulose polymer membrane to be used for more than one type of evaluation.

Non-contact testing of the above types inherently requires probe beams to be incident on the wafer surface at predetermined angles of incidence. For diffraction testing for example it is typical for the probe beam to be incident to the surface of the wafer at an angle of around thirty degrees. Thus for semiconductor wafer testing using the above mentioned tests, the surface area of the window means must be larger than the surface area of the wafer for accessibility by the probe beam if the whole of the wafer surface is to be tested in successive stages.

In modifications (not shown) of the embodiment, window means are included of materials different from that of the embodiment; such materials are mentioned hereunder. However, in each case, a membrane of the window means is of a substantially non-crystalline organic polymer which is satisfactory for use with X-rays.

X-ray diffraction analysis restricts a membrane composition to consist of compounds formed from elements with low atomic numbers. Electrons within electron clouds, which surround atoms are known to have an attenuating effect on X-rays. Electron clouds surrounding atoms of elements having a low atomic number have fewer electrons within their clouds than atoms of elements having higher atomic numbers and hence attenuate X-rays to a lesser degree. Membranes having substantially non crystalline organic polymer membranes tend to be transparent to X-rays and thus may be used satisfactorily in this application.

Absolute thickness of any membrane is a limiting factor for analytical methods using X-rays, infrared or i visible light. The thicker the membrane the greater is the attenuation of both the incident 40 energy and the returned radiant energy 50 from the wafer 20. Bearing in mind this consideration, a variety of polymer materials may be used with attenuation in each case dependent upon the atomic weights of included elements and the practical minimum thickness of the membranes. These materials include poly-propylene, poly-isoprene, poly-vinyl chloride, poly-vinilydene fluoride, poly-carbonate, poly-methyl methacrylate, poly-ethylene, or nitro-cellulose.

The variation in uniformity of thickness across a surface of a membrane can contribute to non-uniform attenuation of incident energy 40 and the returned energy 50. This difficulty can be overcome by first calibrating the analytical test instrument to compensate for previously measured attenuation variances over a membrane's surface using a highly uniform membrane conveniently alleviates much of the effort required to characterize individual membrane attenuation variances and much of the test instrument calibration effort.

What is claimed is:

1. An apparatus for use in performing non contact analytical evaluation of a semiconductor wafer, comprising a sealable container having wall means defining a chamber, which upon sealing the container is then isolated; the sealable container also comprising:

window means into the sealable container, the window means comprising a planar membrane composed solely of a substantially non-crystalline organic polymer, the window means being capable of allowing a probe beam of radiant energy of wavelengths corresponding to X-ray, visible light, or ultra-violet light frequency bands, suitable for non contact analytical evaluation of the semiconductor wafer to pass therethrough into the isolated chamber while non-substantially affecting diffraction and attentuation of the beam and which is capable of passing radiant energy outwardly from the isolated chamber while non-substantially affecting the diffraction and attenuation of the radiant energy;

releasable securing means to secure the window means to the wall means and over an opening to the chamber and to enable removal of the window means to allow for insertion of a wafer through the opening and into the chamber;

sealing means to seal the window means to the wall means when the window means is secured to the wall means; and positioning means for positioning the semiconductor wafer within the isolated chamber in a location aligned with the window means to allow the probe beam of radiant energy to be directed through the window means at the semiconductor wafer and to allow radiant energy to pass outwardly from the semiconductor wafer within the chamber.

2. An apparatus according to claim 1, wherein the sealable container is composed of a charge conducting material.

3. An apparatus according to claim 1 wherein the window means comprises a single window, the window comprising a membrane having a surface area which is larger than the area on the wafer surface which is to be tested.

4. An apparatus according to claim 1 wherein the window means comprises a single window, the window comprising a membrane having a surface area which is larger than the area on the wafer surface which is to be tested.

5. An apparatus according to claim 1 wherein the membrane is capable of passing infra-red light.

6. A method of evaluating a semiconductor wafer by non contact analytical evaluation, comprising the steps of:
   in a first environment, inserting the semiconductor wafer into a chamber within and defined by walls of an open container and positioning the semiconductor wafer in a location within the chamber, the container capable of being selected to isolate the chamber from an outside environment, the container having window means into the chamber, the window means comprising a planar membrane composed solely of a substantially noncrystalline organic polymer, the window means being capable of allowing a probe beam of radiant energy of wavelengths corresponding to X-ray, visible light, or ultra-violet light frequency bands, suitable for non contact analytical evaluation of the wafer, to pass there through while non-substantially affecting diffraction and attenuation of the beam, and which is capable of passing radiant energy outwardly from the isolated chamber while non-substantially affecting diffraction and attenuation of the radiant energy;
   sealing the container to isolate the chamber and the semiconductor wafer from the first environment with the semiconductor wafer aligned with the window means to enable the probe beam of radiant energy to be directed through the window means and at the semiconductor wafer;
   moving the sealed container into a second environment and with the chamber and semiconductor wafer isolated form the second environment;
   passing the probe beam of radiant energy through the window means at the semiconductor wafer during the performance of the non contact analytical evaluation; and
   analyzing radiant energy from the semiconductor wafer which passes outwardly from the wafer within the chamber through the window means to determine structural characteristics about the semiconductor wafer.

7. A method according to claim 6 wherein the window means comprises a single window comprising a membrane having a surface area which is larger than the area of the wafer surface to be tested to expose any part of the wafer to the beam when directed towards the wafer at an angle of less than normal to the wafer surface, the method comprising directing the beam successively from localised position to localised position of the wafer surface and analyzing radiant energy from the wafer at each localized position.

8. An apparatus for use in performing non contact analytical evaluation of a semiconductor wafer, comprising a sealable container having wall means defining la chamber, which upon sealing the container is then isolated; the sealable container also comprising:
   window means into the sealable container, the window means comprising a membrane of nitrocellulose polymer having a thickness of approximately 3.0 microns, the window means being thereby capable of allowing a probe beam of radiant energy of wavelengths corresponding to X-ray, visible light, or ultra-violent light frequency bands, suitable for non contact analytical evaluation of the semiconductor wafer to pass therethrough into the isolated chamber while non-substantially affecting diffraction and attenuation of the beam and which is capable of passing radiant energy outwardly from the isolated chamber while non-substantially affecting the diffraction and attenuation of the radiant energy; and
   positioning means for positioning the semiconductor wafer within the isolated chamber in a location aligned with the window means to allow the probe beam of radiant energy to be directed through the window means at the semiconductor wafer and to allow radiant energy to pass outwardly from the semiconductor wafer within the chamber.

9. An apparatus for use in performing non contact analytical evaluation of a semiconductor wafer, comprising a sealable container having wall means defining a chamber, which upon sealing the container is then isolated; the sealable container also comprising:
   window means into the sealable container, the window means comprising a planar membrane composed solely of a substantially non-crystalline organic polymer, the window means being capable of allowing a probe beam of radiant energy suitable for non contact analytical evaluation of the semiconductor wafer to pass therethrough into the isolated chamber while non-substantially affecting diffraction and attenuation of the beam and which is capable of passing radiant energy outwardly from the isolated chamber while non-substantially affecting the diffraction and attenuation of the radiant energy; and
   positioning means for positioning the semiconductor wafer within the isolated chamber in a location aligned with the window means to allow the probe beam of radiant energy to be directed through the window means at the semiconductor wafer and to allow radiant energy to pass outwardly from the semiconductor wafer within the chamber.

* * * * *